United States Patent [19]

Niedrach

[11] 4,264,424

[45] Apr. 28, 1981

[54] HYDROGEN ION SENSOR HAVING A MEMBRANE SHEATH OF AN OXYGEN ION CONDUCTING CERAMIC

[75] Inventor: Leonard W. Niedrach, Schenectady, N.Y.

[73] Assignee: General Electric Company, San Jose, Calif.

[21] Appl. No.: 84,510

[22] Filed: Oct. 12, 1979

[51] Int. Cl.³ .......................................... G01N 27/46
[52] U.S. Cl. ................................ 204/195 S; 204/1 T
[58] Field of Search ..................... 204/1 S, 195 S, 1 H

[56] References Cited

U.S. PATENT DOCUMENTS

| | | |
|---|---|---|
| 3,402,078 | 9/1968 | Spacil . |
| 3,404,040 | 10/1968 | Mitoff et al. . |
| 3,436,269 | 4/1969 | Mitoff . |
| 3,481,780 | 12/1969 | Mitoff . |
| 3,481,855 | 12/1969 | Kolodney et al. ............... 204/195 S |
| 3,671,414 | 6/1972 | Grubb . |
| 3,673,069 | 6/1972 | Niedrach et al. . |
| 3,709,810 | 1/1973 | Grubb et al. . |
| 3,740,326 | 6/1973 | Grubb . |
| 3,776,831 | 12/1973 | Roy et al. ......................... 204/195 S |
| 3,791,954 | 2/1974 | Noda et al. ....................... 204/195 S |
| 3,816,269 | 6/1974 | Wilder ............................... 204/195 S |
| 3,871,981 | 3/1975 | Flais et al. ........................ 204/195 S |
| 3,883,408 | 5/1975 | Kim et al. ......................... 204/195 S |
| 3,911,901 | 10/1975 | Niedrach et al. . |
| 4,096,048 | 6/1978 | Matsumoto et al. ............. 204/195 S |
| 4,179,491 | 12/1979 | Howe et al. ...................... 204/195 S |
| 4,183,798 | 1/1980 | Esper et al. ...................... 204/195 S |

FOREIGN PATENT DOCUMENTS

| | | |
|---|---|---|
| 2735789 | 3/1978 | Fed. Rep. of Germany ....... 204/195 S |
| 2808621 | 9/1978 | Fed. Rep. of Germany ....... 204/195 S |
| 53-46475 | 12/1978 | Japan ................................... 204/195 S |

OTHER PUBLICATIONS

"Calcia-Doped Ceria Ceramic Tubes for Low Temperature Oxygen Sensors" by Dirstine et al., *Ceramic Bulletin*, vol. 58, No. 8 (1979), pp. 778-783.
"The Activities of Oxygen in Liquid Copper and its Alloys with Silver and Tin", Trans. of the Met. Soc. of AIME, vol. 245, Aug. 1969, pp. 1721-1722.
"Electrochemical Measurements of Oxygen in Silver and Copper", Electromotive Force Measurements in High Temperature Systems, Alcock, 1968, pp. 29-33.
Kiukkola et al., "J. of the Electrochemical Soc.", Jun. 1957, pp. 379-387.

*Primary Examiner*—T. Tung
*Attorney, Agent, or Firm*—Ivor J. James, Jr.; Samuel E. Turner; Raymond G. Simkins

[57] ABSTRACT

A hydrogen ion sensor comprising in combination a gas impervious membrane sheath of an oxygen ion conducting ceramic, an electrochemical system partially contained therein, a terminal external to the ceramic sheath electrically connected to the electrochemical system and means for sealing the interior of the ceramic sheath from the ambient, the electrochemical system providing a fixed steady electrical potential that varies only with temperature between the inner surface of the ceramic sheath and the terminal.

16 Claims, 4 Drawing Figures

HYDROGEN ION SENSOR HAVING A MEMBRANE SHEATH OF AN OXYGEN ION CONDUCTING CERAMIC

BACKGROUND

This invention relates to hydrogen ion, or pH, sensors. Sensors are employed to determine the content of a specific substance in a fluid or atmosphere. For example, a sensor can be employed to determine the content of oxygen, or carbon dioxide in a sample, or its content of hydrogen ions or other ions in solution.

Ion sensors are known in the prior art for measuring the hydrogen ion activity or pH of a sample. Such a sensor, for example the well-known glass electrode, is used in conjunction with a reference electrode. When both are immersed in a solution the potential difference between the two electrodes is a function of the concentration of hydrogen ions in the solution.

Sensors such as those previously described are normally utilized for measuring ion concentrations of liquids at approximately ambient temperature conditions, or perhaps at somewhat higher temperatures ranging up to about 100°–150° C. levels. However, in connection with certain recent innovations, such as nuclear reactors, geothermal wells and other operations entailing relatively high temperature fluid systems, there has often been interest in, or a need for, measuring the pH of water at temperatures in the order of about 300° C., or higher.

Conventional glass-containing electrodes are not suitable for such high temperature service because of the accelerated rates of attack and dissolution of glass occurring at such temperatures. Other pH sensors based upon reversible electrode couples, for instance the conventional hydrogen electrode, the oxygen electrode, the palladium hydride electrode and various metal—metal oxide couples, although potentially useful under certain limited conditions, lack the general versatility of electrodes having glass membranes. Accordingly, some sensor systems require the presence of reactive gases in known concentrations, many systems are poisoned by impurities such as sulfides and most sensor systems are influenced by other reduction—oxidation couples in the system.

One of the virtues of a membrane in a membrane type electrode (e.g. the glass electrode) is that, unlike the above constructions, they are normally insensitive to changes in the reduction-oxidation environment and are resistant to poisoning by impurities such as sulfides. Membrane materials can often be found that exert no significant influence on the environment.

SUMMARY OF THE INVENTION

This invention comprises a new and improved pH sensor for hydrogen ions that is suitable for use in fluids or solutions at relatively high temperatures, and comprises a sheathing material having oxygen ion conducting properties that serves as the hydrogen ion sensing element.

It is a primary object of this invention to provide a novel and improved hydrogen ion sensor which is effective and enduring in a variety of services and extreme conditions.

It is also an object of this invention to provide a new, high temperature service hydrogen ion sensor capable of entering into equilibrium with hydrogen ions in an aqueous phase, and having sufficient conductivity for use with conventional detection equipment and apparatus.

It is a further object of this invention to provide a novel, high temperature service hydrogen ion sensor of ample stability to minimize drift and provide long performance life.

It is an additional object of this invention to provide a durable and accurate hydrogen ion sensor that is capable of effective and enduring operation in relatively high temperature fluids and atmospheres.

The pH sensor for hydrogen ions of this invention comprises a combination of a gas impervious membrane sheath, an electrochemical system partially contained in the sheath and a terminal external to the sheath, the electrochemical system providing a fixed steady electrical potential that varies only with temperature between the inner surface of the sheath and the terminal, the sheath being composed of an oxygen ion conducting ceramic. Examples of electrochemical systems useful in the sheath are (1) a halide (other than fluoride) solution containing a controlled (i.e. predetermined and stable) concentration of hydrogen ions, a silver-silver halide (other than fluoride and the same as the halide of the solution) electrode and an electrically conducting lead in electrical contact with the electrode and extending from the sheath, the halide solution being in contact both with the inner surface of the sheath and with the electrode and (2) a mixture of solid particles, which can be a metal and an oxide thereof or two different oxides of the same metal, and an electrically conducting lead extending from the sheath, the mixture being in contact both with the inner surface of the sheath and the lead.

DETAILED DESCRIPTION OF PREFERRED EMBODIMENTS

Figure 1:
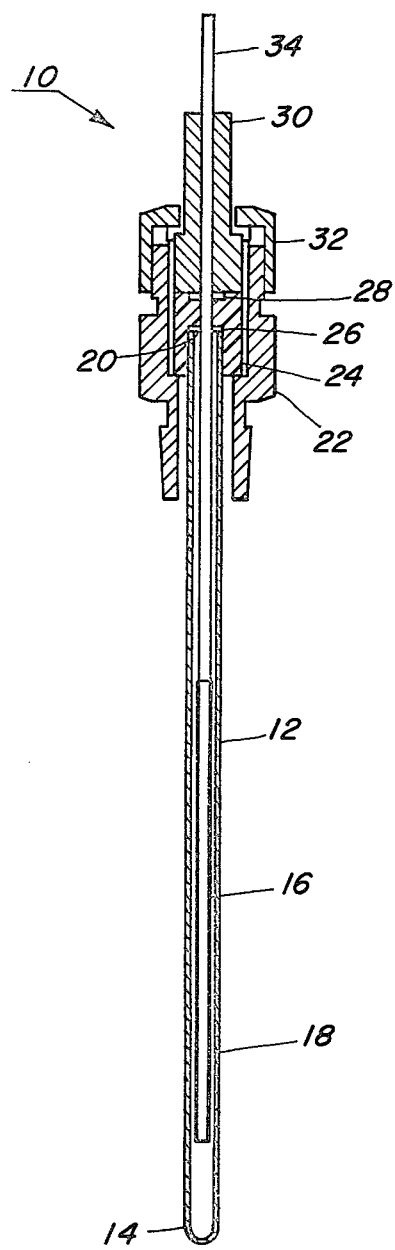
FIG. 1 comprises a cross-sectional view of one embodiment of a pH sensor of this invention.

The new and improved hydrogen ion sensor of this invention is constructed with a membrane sheath or housing component comprising a durable and high temperature-resistant oxygen ion conducting ceramic membrane. It has not been previously recognized that oxygen ion conducting ceramics can function as membranes for hydrogen ion sensing elements.

An especially suitable and preferred oxygen ion conducting ceramic for the practice of this invention is stabilized zirconium oxide. Solid doped thoria and ceria are also apt solid oxygen ion conducting metal oxides for use in the invention. The mobile oxygen ions in such ceramics or metal oxides are able to enter into equilibrium with the hydrogen ions in a solution to be measured for hydrogen ion concentration, and they also serve as the current carriers within the ceramic phase. The ionic conductivities of these ceramics are established properties thereof which are known to the art.

A preferred oxygen ion conducting metal oxide or ceramic for a membrane structure or sheath in the practice of this invention comprises a solid oxide of zirconium, containing a stabilizing agent. Solid stabilized zirconia is a solid oxygen ion conducting ceramic material or oxide compound with a cubic crystal structure consisting of zirconia to which is added at least one or a combination of several specific oxides such as calcium oxide, yttrium oxide, or a mixture of rare earth oxides. An example of one preferred oxygen ion conducting ceramic for the membrane sheath of this invention comprises solid zirconia containing about 8 to about 17 weight percent of yttrium oxide ($Y_2O_3$) as a stabilizing agent. Other compositions of stabilized zirconia, which are employable for the oxygen ion member and as the oxygen ion conducting metal oxide or ceramic are disclosed in "Oxygen Ion Conductors" by Dell and Hooper is SOLID ELECTROLYTES, Hagenmuller and Van Gool, eds., Academic Press, 1978, pp. 291–312, and in "The Electrical Properties of Solid Oxide Electrolytes" by Etsell and Flengas in Chem. Reviews, 70, 339–376 (1970).

Other oxides or ceramics, such as doped thorium oxide, doped cerium oxide, doped lanthanium oxide, and related oxygen ion conducting ceramics known in the art may also be used in the practice of the subject invention. For instance, lanthanum oxide doped with strontium oxide and cerium oxide doped with gadolinium oxide or calcium oxide would have low resistivities at likely temperature levels for the practice of this invention and therefore comprise useful ceramic materials for membrane bodies or sheaths in the sensors of this invention, see Chapter 18 entitled "Oxygen Ion Conductors" by Dell and Hooper, in *SOLID ELECTROLYTES, supra.*

In general it is desirable that the transport number for the oxygen ion be high and close to 1.0. in particular the transport number for electron and positive hole conduction should be an order of magnitude lower than that for the oxygen ion conduction and preferably at least two orders of magnitude lower. This requirement may limit the applicability of some oxygen ion conducting ceramic membranes to systems where the reduction-oxidation potential of the environment remains within a restricted range because the relative values of the transference numbers change with this potential. Thus in the presence of relatively high activities of oxygen, yttria doped thoria has an excessive positive hole conductivity, particularly at elevated temperatures. This type of variation of conductivity domain for oxygen ion conducting ceramics is discussed by J. W. Patterson in the Journal of the Electrochemical Society, Vol. 118, pp. 1033–1039 (1971).

Stabilizing or doping agents for use with the oxygen ion conducting ceramics or oxides in this invention comprise yttrium oxide, calcium oxide, magnesium oxide, scandium oxide, gadolinium oxide and other known and appropriate stabilizing oxides from group two and three of the periodic table, employed either singly or in combinations.

The stabilizing agents can be included with the oxygen ion conducting ceramic in effective amounts of about 5 to 46 mole percent.

The oxygen ion conducting metal oxide or ceramic membrane sheath or housing for the pH sensors of this invention can be prepared from powders of stabilized zirconia or other suitable ceramics using the plasma spraying procedures described in U.S. Letters Pat. No. 3,429,962 to C. W. Krystyniak. Alternatively slip casting, isostatic pressing or other conventional techniques for ceramic fabrication can be used. Also, certain of the ceramics, such as stabilized zirconia, can be purchased commercially in common configurations such as tubular. In any case, the membrane sheaths or housings should be considered commercially to be gas impervious, and the transference numbers for oxygen ions, electron and positive hole transport should comply with the conditions specified hereinbefore. Also, the conductivity of the membrane sheating should be adequate at the particular operating temperature to meet the requirements of the instrumentation utilized.

According to one embodiment of this invention, a hydrogen ion sensor is constructed with an indirect junction as the electrochemical system. Such an indirect junction can comprise an oxygen ion conducting ceramic tube or sheath which is closed at one end, a silver-silver halide (other than the fluoride) electrode positioned at least partially within the tube or sheath, an electrical lead in electrical contact with the electrode, and a solution of controlled hydrogen ion concentration containing at least one halide salt (other than a fluoride) partially filling the tube or sheath and in contact with the silver-silver halide electrode. (It is to be noted that because water expands significantly with increasing temperature, a substantial volume of free space must be allowed within a sensor that is assembled at ambient temperature and is operated at elevated temperatures in the order of about 300° C.) The end of the ceramic tube or sheath opposite that closed, is blocked off with a sealing means and with the electrical lead extending out therethrough. This type of internal junction is typical of those used with conventional glass electrodes in which silver-silver chloride electrodes are employed with buffered saline solutions; cf. "Determination of pH-Theory and Practice", by Roger G. Bates, John Wiley and Sons, Inc., 1964.

In another embodiment of this invention the sensor is constructed with a direct junction as the electrochemical system whereby the internal aqueous solution and the silver-silver halide electrode are replaced by a non-aqueous reduction-oxidation couple such as a metal-metal oxide couple in direct contact with the ceramic tube or sheath and also in contact with an electrical lead. Preferred metal-metal oxide couples comprise a mixture of copper and copper oxide, or of mercury containing mercury oxide, but other metal-metal oxide couples can be utilized. Alternatively, a mixture of two different oxides of a single metal can also be used in the direct junction, for example, ferrous oxide-magnetite or magnetite-hematite combination. If appropriate, some carbon or other inert conducting material can be added if an oxide is not sufficiently conductive. This type of internal connection has been used successfully in the fabrication of the well-known stabilized zirconia high temperature oxygen sensors; cf. "Reference Electrodes" by J. Hladik, Chapter 20 in Physics of Electrolytes edited by J. Hladik, Academic Press, 1972.

The method of forming a direct junction can also be varied. For example, a thin coating of copper or silver can be applied on the inside surface of the ceramic sheath or tube by electroless deposition or by sputtering, and an electrical contact made therewith through a spring connector or with a conducting resin binder. In such embodiments, the oxide phase can be formed by controlled heating in an oxidizing atmosphere or by anodizing through the ceramic of the sheath or tube itself. In that electrometers drawing very low currents can be used for the pH measurements, only minimal amounts of an oxide are required for long life.

Another alternative for an internal connection within the ceramic sheath or tube is a suitable salt, either solid or molten, in contact with an appropriate electrode, such as an oxyhalide with a halided silver wire to establish a fixed potential with the wire and the oxygen ions of the ceramic.

The ceramic membrane sheaths of this invention, and the hydrogen ion-sensors embodied therein can be constructed in any suitable shape or configuration for its intended service. For instance, in addition to a tubular or cylindrical structure, the ceramic membrane sheath or container can be bulbous or spherical, or of any apt geometry. In such constructions, thick and thin film fabrication techniques can be used to fabricate the sensor sheath or housing on shaped supports or forms.

Referring to the drawings, FIG. 1 illustrates one embodiment of a hydrogen ion-selective sensor of this invention. Hydrogen ion-selective sensor 10, comprises a tubular sheath 12 of an oxygen ion conducting ceramic such as stabilized zirconium oxide. Tubular sheath 12 is closed at one end 14. An internal electrode 16 of a silver wire with a silver halide (other than a fluoride) coating on at least a portion thereof is generally concentrically positioned within the sheath 12 and in contact with an aqueous solution of an electrolyte 18 having a controlled hydrogen ion concentration and at least one halide salt (other than a fluoride) occupying the area intermediate the sheath 12 and electrode 16. The open end 20 of tubular sheath 12 is capped with an assembly of a pressure fitting 22, and including a polytetrafluoroethylene (TEFLON) seal 24, silver disks 26 and 28, alumina insulator 30, and cap 32. Lead wire 34 makes contact with or is an integral part of the electrode 16 and extends therefrom out through the pressure fitting assembly.

Figure 2:
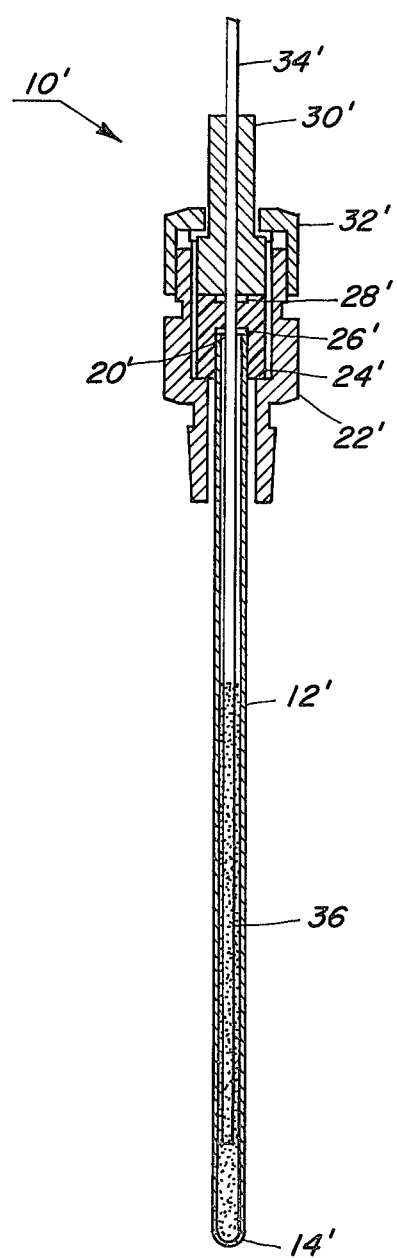
FIG. 2 comprises a cross-sectional view of another embodiment of a pH sensor of this invention.

In an alternative embodiment illustrated in FIG. 2 of the drawing, the hydrogen ion selective sensor 10', comprises a tubular sheath 12' of an oxygen ion conducting ceramic, having a closed end 14'. Sheath 12' contains a mixture 36 of a powdered metal and its oxide in contact with both the membrane sheath 12' of ceramic and lead wire 34'. The open end 20' of sheath 12' is likewise capped with an assembly of a pressure fitting 22', and including a polytetrafluoroethylene (TEFLON) seal 24', metal disks 26' and 28', alumina insulator 30', and cap 32'. Lead wire 34' extends from contact with the mixture 36 of metal and its oxide out through the pressure fitting assembly.

The operation of membrane and other types of pH sensors and the procedures used for their calibration are set forth in detail in the literature, for example "Determination Of pH-Theorgy And Practice", by Roger G. Bates, John Wiley and Sons, Inc., (1964). Briefly, however, a pH sensor of the membrane type is devised by employing a membrane material having a composition such that it can enter into electrochemical equilibrium with the phase to be measured, usually aqueous and so considered in the following discussion, such that ionic species of interest of the phase is the potential determining species at the interface.

When the membrane material is an oxygen ion conducting ceramic of this invention, the mobile oxygen ions in the ceramic attain equilibrium with the hydrogen ions in the solution, which are thus the potential determining species. This becomes clearer if we consider other species in the solution for which the pH is being measured and their equilibria with the hydrogen ions. In particular we focus on oxygenated ions which are involved in the following equilibria

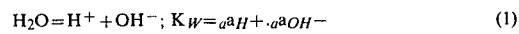

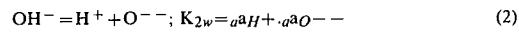

and

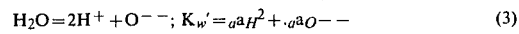

While the first dissociation of water, Equation 1, is of general importance and its equilibrium constant, $K_w$, is well established, the second dissociation to produce $O^=$ species, Equations 2 and 3, is not normally of interest because the magnitude of this dissociation is negligible for practical purposes. Nevertheless, it provides a useful tool in considering the interface potential.

When such an oxygen ion conductin membrane is in equilibrium with an aqueous phase the electrochemical potential of oxygen ions is equal in the membrane and the aqueous phase. That is the aqueous phase is given by

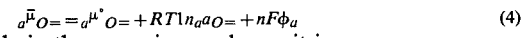

while in the ceramic membrane it is

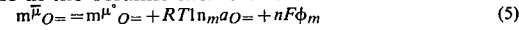

where the barred terms are the electrochemical potentials, the unbarred are the standard chemical potentials, $_aa_{O=}$ and $_ma_{O=}$ are the oxygen ion activities in the two phases $\phi_a$ and $\phi_m$ are the inner or galvani potentials of the two phases, n is the charge on the ion of interest and the remaining terms have their usual meaning. At equilibrium we then have for the potential drop at an interface $$\Delta\phi_i = \phi_m - \phi_a = \qquad (6)$$
$$\frac{1}{nF} (_a\mu°_{O=} - _m\mu°_{O=} - RT\ln {_ma_{O=}} + RT\ln {_aa_{O=}})$$

Substituting Equation 3 and 6 and bearing in mind that for the O_ ion n = -2 we obtain $$\Delta\phi_i = \qquad (7)$$
$$\frac{-1}{2F} (_a\mu°_{O=} - _m\mu°_{O=} - RT\ln {_ma_{O=}} + RT\ln K_w' - 2RT\ln {_aa_{H+}}$$

Since, $_ma_{o=}$, the O= activity in the membrane is constant $$\Delta\phi_i = K + \frac{RT}{F} \ln {_aa_{H+}} \qquad (8)$$

Then from the definition of pH as the negative of the logarithm of the hydrogen ion activity, and converting to the base 10

$$\Delta\phi_i = K - 2.303 \frac{RT}{F} pH \qquad (9)$$

Figure 3:
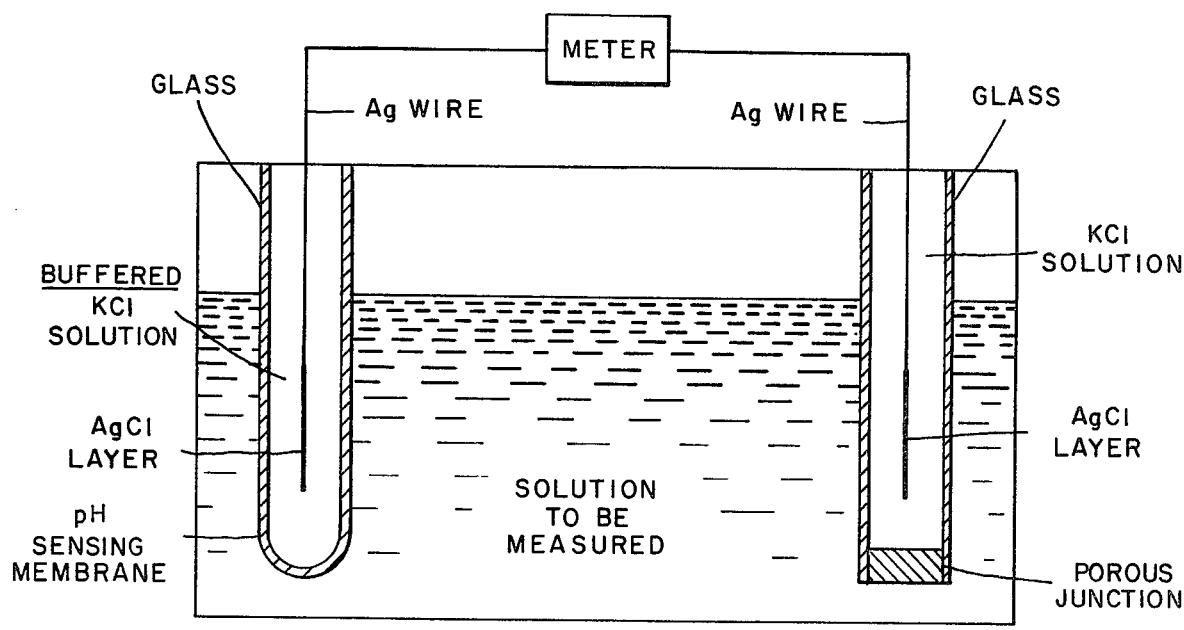
FIG. 3 comprises a schematic diagram illustrating equipment and an electrochemical system for measuring pH with which the pH sensor of this invention can be employed.

In the use of a membrane electrode for the measurement of pH it is normally employed in an arrangement as shown in FIG. 3 in which an aqueous solution containing a halide salt and a controlled hydrogen ion concentration is contained within the tubular membrane. In contact with the inner solution is a silver wire coated with a silver halide corresponding to the halide in solution. Because of the constant composition of the internal solution the potential drop at the interface between the solution and the halided silver wire is fixed by the halide ion concentration. The potential drop at the interface between the solution and the membrane is fixed by the hydrogen ion concentration of the inner solution by much the same mechanism as that involved on the outer surface.

In order to make appropriate potential measurements that can be related to the pH of the solution being measured a suitable second electrode or reference electrode is required. This is shown on the right of the diagramed system of FIG. 3 and contains a solution of a halide salt in contact with a silver wire coated with a silver halide corresponding to the halide in solution. This again establishes a fixed potential since the concentration of the salt in the reference electrode is maintained constant during use. Contact of the reference electrode with the solution to be measured is by means of a liquid junction through a porous medium. The salt in the reference electrode solution is chosen so that the transference numbers of the cationic and anionic species are essentially equal and ~0.5. Under these conditions the junction potential is reasonably constant and small and may therefore be neglected in the pH measurements. Normally KCl solutions are used in reference electrodes because of the similarity of the transference numbers of the two ions. (Reference electrodes and liquid junction potentials are discussed thoroughly by Bates, loc cit.)

Under these conditions, then, it is apparent that as the pH of the solution being measured changes all potentials in the measuring system remain constant with the exception of the interface potential of the membrane in contact with the solution being measured. Then, by using a system that has been properly calibrated as explained by Bates it is possible to derive the pH of an unknown solution from the voltage reading obtained on a meter. Normally a very high impedance meter such as an electrometer is used for this purpose, and when a properly functioning system is employed a linear relationship is found between the pH and the voltage.

The same situation prevails, of course, when a direct junction contact is made to the inner surface of the tubular membrane. In this case the activities of the oxidant and reductant phase remain fixed at the interface and a constant potential is maintained. Readings from such a sensor may differ by a constant amount from a corresponding system employing an aqueous internal, but the linear relationship between pH of the unknown and the output voltage on a meter will still be obtained.

In performing test experiments in connection with the EXAMPLES below several different physical arrangements were employed. Initial tests were performed with the membranes in the form of open end tubes i.e., open at the upper end, much as illustrated in FIG. 3. In these cases the reference electrode was that of an INGOLD ® Electrodes, Inc. Series 514 "combination pH electrode" (a combined glass electrode/reference electrode in a unitized structure that is available from commercial suppliers of glass electrodes for pH measurement). To determine the performance of the new sensors their response was compared with that of the glass electrode portion of the combination electrode measured against the same reference.

In these tests the internal electrolyte in some of the zirconia tubes was prepared by dissolving one pH 7.0 pHydrion buffer capsule in 100 ml 0.1 m NaCl. In other cases this electrolyte was diluted by a factor of 10. An insulated, chlorided silver wire served as the internal electrode in the conventional arrangement which parallels that of a typical commercial glass electrode. The reference electrode was that of an INGOLD ® combination electrode, the glass portion of which was used for comparison measurements. The electrodes were inserted in a 150 cc beaker that also contained a magnetic stirring bar. All of the electrodes were then equalibrated with solutions of different pH including HCl solutions, NaOH solutions and phosphate buffers. Measurements were made with an Instrumentation Laboratory Model 245 pH meter with the aid of an Orion Model 855 Electronic Switch. Alternatively Keithley Electrometer Models 602 and 616 have been employed in place of the pH meter.

In order to make measurements at 285° C., it was necessary to devise structures that could be inserted into a pressurized autoclave. The structures finally adopted are shown in FIGS. 1 and 2 of the drawings. The entire units were then mounted in the lid of a 1 liter autoclave that also held an insulated platinized-platinum wire and a reference electrode consisting of a chlorided silver wire immersed in a 0.01 m KCl solution within a zirconia tube containing a porous passage near the end of the tube. In other tests an alternative reference electrode of the general type described by M. Indig in CORROSION, Vol. 34, page 3, 1978 was used.

Figure 4:
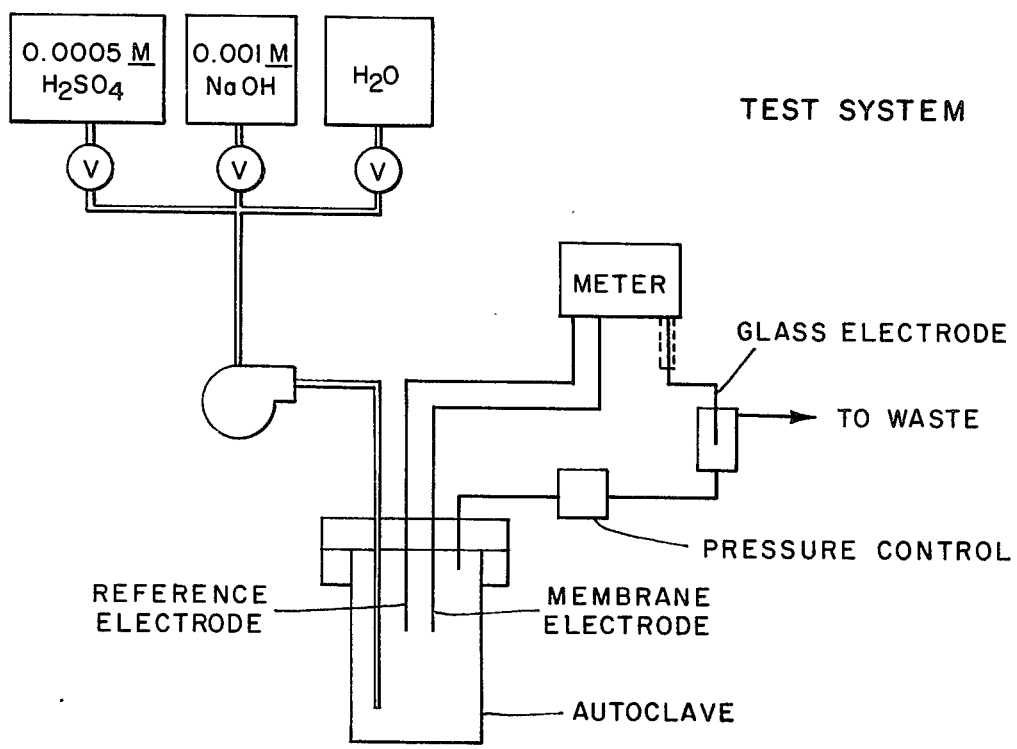
FIG. 4 comprises a diagram of a test system and means for measuring and evaluating pH determinations.

The test system is shown in FIG. 4. Provision is made to pump water, acid or base into the heated and pressurized autoclave. This enables us to slowly "titrate" the pH back and forth with acid and base or to introduce rapid chamnges by introducing aliquots of more concentrated reagent. Since a well-established comparison standard (like the commercial glass electrode used in the measurements at ambient temperature) is not available for 285° C. it was elected to compare the response of the membrane to that of an "oxygen electrode" formed by the platinized platinum wire in contact with the reagents that had all been saturated with air at ambient temperature before entering the autoclave. Under these conditions of constant oxygen concentration, the oxygen electrode can serve as a pH sensor because hydrogen ions are involved in the potential determining reaction

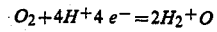

$$O_2 + 4H^+ + 4e^- = 2H_2 + O$$

A similar arrangement was used for tests conducted at 90°–95° C., but in these cases the electrodes including an INGOLD ® combination electrode were mounted within an autoclave at ambient pressure. Solutions of various pH were then pumped through the autoclave in the same fashion as used for the higher temperature measurements. The INGOLD ® glass electrode rather than the platinized-platinum oxygen electrode was used as the comparison standard at 90°–95° C.

Examples of hydrogen ion sensors made in accordance with my invention are set forth below:

EXAMPLE 1

A hydrogen ion sensor was formed using an open tube in accordance with the above description and as generally shown in FIG. 3 of the drawings. The approximately 5/16 inch outside diameter, by 1/32 inch wall thicknes by 8 inch long zirconia tube stabilized with about 15 weight percent yttria was prepared using plasma spraying procedures described in U.S. Pat. No. 3,429,962, supra. The tube was filled to a depth of about two inches with a solution of 0.1 m HCl. An insulated silver wire was stripped of insulation for a length of about 1 cm at either end. One of these ends was chlorided by anodization for several minutes with the wire immersed in 0.1 m HCl solution. The chlorided end was immersed in the solution within the sensor and served as the internal electrode in the sensor.

After fabrication the sensor was tested by immersing it in acidified solutions of various strengths contained in beakers as generally shown in FIG. 3 and measuring its potential against a commercial reference electrode manufactured by Beckman Instruments, Inc. The entire system including the battery, operated keithley 602 electrometer used for the measurements was placed within a faraday cage for the measurements which were made at ambient temperature, about 25° C. Over a pH range from approximately 1 to 4 the average response of the membrane sensor was linear and about 46.5 mv/pH unit. This corresponds to a sensor response that is 78.6 percent of theoretical, which establishes that it was functioning as a hydrogen ion sensor at 25° C.

EXAMPLE 2

Two additional hydrogen ion sensors were formed generally as in EXAMPLE 1 except that the ¼ inch outside diameter, by 1/32 inch wall thickness by 6 inch long zirconia tubes were stabilized with 8.0 weight percent yttria and were prepared by slip casting by the Ceramics Products Division of the Corning Glass Works from whom they were purchased, and the internal electrolyte in the tubes was prepared by dissolving one pH 7.0 pHydrion buffer capsule in 100 ml 0.1 m NaCl.

After fabrication these sensors were tested at ambient temperature, about 25° C., by immersing them in solutions over the pH range established at the extremes by 0.1 M NaOH and 2 m HCl. The solutions were contained in beakers as generally shown in FIG. 3, and the potentials of the sensors were measured against a reference electrode. Also inserted into the beakers was an INGOLD ® combination pH electrode, the glass electrode of which served as a comparison standard and the reference arm of which served as the reference electrode for both the glass electrode and the membrane sensors during the measurements. The potential measurements were performed in a faraday cage with a Keithley Model 602 electrometer. The responses of the sensors to changes in pH were essentially linear and 98.9 and 99.3 percent of that of the commercial glass electrode, respectively, thereby establishing that the two sensors were functioning as hydrogen ion sensors.

EXAMPLE 3

An additional hydrogen ion sensor was formed generally as in EXAMPLE 2 using a zirconia tube stabilized with 8.0 weight percent yttria and again purchased from the Ceramics Products Division of the Corning Glass Works. In this case the internal electrolyte in the sensor was equivalent to that used in EXAMPLE 2, but reduced in concentration by a factor of 10.

This sensor was tested at about 95° C. while submerged in solutions in the autoclave in a system as generally shown in FIG. 4. At 95° C. it was not necessary to pressurize the system and the sensor was simply inserted through the lid of the autoclave using a Teflon fitting while the open end of the tube was covered with a loose fitting Teflon cap to minimize evaporation. The performance was again compared with that of an IN-GOLD ® combination pH electrode as the pH of the solution in the autoclave was varied over the range established at the extremes by 0.0005 m $H_2SO_4$ and 0.001 m NaOH. On the basis of seven data sets obtained over a period of 3.8 days the response of the sensor was essentially linear and 91.8 percent of that of the glass electrode, which establishes that it was functioning as a hydrogen ion sensor at 95° C.

During these measurements the response of the oxygen electrode formed by dissolved oxygen in the test solutions at a platinized platinum wire immersed in the same solution was also compared with that of the glass electrode. Its response during the same test period was also essentially linear and 87.8 percent of that of the glass electrode, which establishes that it too was functioning as a hydrogen ion sensor at 95° C. Having established this performance for the oxygen electrode it is to be expected that performance at higher temperature (e.g. 285° C.) will be even better, because of improved electrode kinetics at higher temperatures. It is for this reason that oxygen electrodes have been used as the comparison standard in some of the examples which follow.

EXAMPLE 4

Two additional hydrogen ion sensors were formed generally as in EXAMPLE 3 except that the ⅜ inch outside diameter, by 0.050 inch wall thickness by 6 inch long zirconia tubes were stabilized with 8.0 weight percent yttria and were prepared by isostatic pressing by the Coors Porcelain Co. from whom they were purchased.

These sensors were tested at 95° C. using the procedures employed in EXAMPLE 3. On the basis of five data points obtained over a day's operation the responses of these sensors were essentially linear and 97.4 and 93.8 percent of that of the glass electrode, respectively, which establishes that they were functioning as hydrogen ion sensors at 95° C.

EXAMPLE 5

An additional hydrogen ion sensor was formed generally as in EXAMPLE 2 using a zirconia tube stabilized with 8.0 weight percent yttria purchased from the Ceramics Products Division of the Corning Glass Works. In this case, however, the high pressure Conax fitting was applied as generally shown in FIG. 1.

The sensor was tested while submerged in solutions in the autoclave in a system as generally shown in FIG. 4. In this case the tests were performed at 285° C. so that it was necessary to pressurize the system; a control pressure of 1200 PSI was employed. Since no commercial glass standard is available for operation under the conditions of this example, the oxygen electrode formed at a platinized platinum wire by oxygen dissolved in the test solutions was used as the comparison standard. This is reasonable since it had been established in EXAMPLE 3 that such an electrode serves as a pH sensor even at 95° C. The oxygen level in these solutions was that established by purging them with air at ambient temperature and pressure before they entered the autoclave. The potentials of both the sensor and the oxygen electrode were measured against a high temperature reference electrode of the general type described by Indig, loc. cit. On the basis of 13 data sets obtained over a period of 8.8 days with the solution pH established at the extremes by 0.0005 m $H_2SO_4$ and 0.001 m NaOH the response of the sensor was essentially linear and 92.9 percent of that of the oxygen electrode, which establishes that it was functioning as a hydrogen ion sensor at 285C.

EXAMPLE 6

An additional hydrogen ion sensor was formed generally as in EXAMPLE 5 except that a zirconia tube stabilized with 16.9 weight percent yttria purchased from the Ceramics Products Division of the Corning Glass Works was used.

This tube was tested generally as in EXAMPLE 5 at 285C. Performance was again compared with that of the oxygen electrode. On the basis of twelve data sets obtained over a period of 5.7 days the response of the sensor was 96.4 percent of that of the oxygen electrode, which establishes that it was functioning as a hydrogen ion sensor at 285C.

EXAMPLE 7

An additional hydrogen ion sensor was formed generally as in EXAMPLE 5 except that a zirconia tube stabilized with 7.5 weight percent calcia purchased from the Ceramics Products Division of the Corning Glass Works was used.

This tube was tested generally as in EXAMPLE 5 at 285° C. and performance was again compared with that of the oxygen electrode. On the basis of twelve data sets obtained over a period of 5.7 days the response of the sensor was essentially linear and about 43 percent of that of the oxygen electrode, which established that the sensor was functioning as a hydrogen ion sensor at 285° C.

EXAMPLE 8

A hydrogen ion sensor was formed generally as in EXAMPLE 3 except that the internal aqueous electrolyte and chlorided silver wire were replaced by a direct junction type internal consisting of a copper wire held in place by a mixture of 50 weight percent copper powder and 50 weight percent cuprous oxide packed to a depth of three inches in the bottom of the tube. Because the tests were not to be performed at elevated pressures the tube was closed on the top with a simple Teflon cap.

This sensor was tested as generally outlined in EXAMPLE 3, at 95° C. On the basis of nine data sets obtained over a period of 6.1 days the response of the sensor was essentially linear and 100.8 percent of that of the INGOLD ® glass electrode, which establishes that it was functioning as a hydrogen ion sensor at 95° C.

EXAMPLE 9

A hydrogen ion sensor was formed generally as in EXAMPLE 8 except that the direct junction type internal connection consisted of mercury containing mercury oxide contained to a depth of three inches within the tube and into which a platinum wire was immersed for external connection to the measuring equipment.

This sensor was tested as generally outlined in EXAMPLE 3 at 95° C. On the basis of five data sets obtained over a period of 2.2 days the response of the sensor was essentially linear and 102.7 percent of that of the INGOLD ® glass electrode, which established that it was functioning as a hydrogen ion sensor at 95° C.

EXAMPLE 10

A hydrogen ion sensor was formed generally as in EXAMPLE 8. In this case, however, a high pressure Conax fitting was applied as generally shown in FIG. 2. The sensor was tested generally as in EXAMPLE 5 at 285° C. On the basis of ten data sets obtained over a period of 3.7 days the response of the sensor was essentially linear and 96.1 percent of that of the oxygen electrode, which establishes that it was functioning as a hydrogen ion sensor at 285° C.

EXAMPLE 11

The sensor of EXAMPLE 5, in an extension of the tests conducted in the same EXAMPLE 5, was further examined for its stability as the reduction-oxidation potential of the test environment was changed. This was accomplished by equilibrating the feed solution, 0.0005 m $H_2SO_4$, with nitrogen rather than air. Under these conditions the reduction-oxidation potential of the solution gradually declined as dissolved oxygen was gradually displaced from the solution. While this resulted in a gradual decline in the potential of the oxygen electrode, there was no change in the potential of the sensor as measured against the reference electrode.

Eventually the oxygen level in the solution fell sufficiently that it could no longer maintain a protective passive film on the walls of the autoclave. At this point corrosion of the autoclave increased and hydrogen was released into the water. This resulted in a marked drop in the reduction-oxidation potential of the solution and the potential of the platinized platinum electrode shifted from that of an oxygen electrode to that of a hydrogen electrode—several hundred millivolts. In contrast, apart from a minor brief transient, the potential of the sensor remained steady against the reference electrode as it should, because the acidity of the solution was not changed in this experiment. This demonstrates that the new sensor is indeed functioning as a membrane electrode and showing the anticipated independence of the reduction-oxidation potential of the solution.

What is claimed is:

1. In a hydrogen ion sensor comprising a gas impervious membrane sheath, a terminal located external to said sheath and an electrochemical system electrically interconnecting the inner surface of said sheath and said terminal to establish a fixed steady electrical potential between said inner surface and said terminal that varies only with temperature, the improvement wherein said sheath is constructed of an oxygen ion conducting ceramic and said electrochemical system consists of a silver-silver halide electrode located in said sheath, an electrically conducting lead in electrical contact with said terminal and a liquid solution of predetermined stable hydrogen ion concentration containing a halide salt, said solution being in contact with a portion of the inner surface of said sheath and with said electrode, the halide of said electrode and said solution being the same and being selected from the group consisting of chloride, bromide and iodide.

2. The hydrogen ion sensor of claim 1, wherein the sheath is composed of at least one oxygen ion conducting ceramic selected from the group consisting of stabilized zirconium oxide, doped thorium oxide, doped cerium oxide and doped lanthanum oxide.

3. The hydrogen ion sensor of claim 1, wherein the oxygen ion conducting ceramic is stabilized zirconium oxide.

4. The hydrogen ion sensor of claim 3, wherein the stabilizing agent for the zirconium oxide is selected from the group consisting of yttria, scandia, calcia and magnesia.

5. The hydrogen ion sensor of claim 1, wherein the halide is chloride.

6. In a system for determining the concentration of hydrogen ions in a liquid medium comprising in combination a hydrogen ion sensor, a reference electrode external to and spaced from said sensor and means for measuring voltage electrically connected between a terminal of said sensor and said reference electrode, said sensor and said reference electrode each being in contact with said liquid, said reference electrode comprising an electronic conductor in contact with an ionic solution and said ionic solution in turn being in contact with said liquid; said sensor comprising a gas impervious membrane sheath, an electrochemical system and said terminal, said terminal being external to said sheath and said electrochemical system electrically interconnecting the inner surface of said sheath and said terminal to establish a fixed steady electrical potential between said inner surface and said terminal that varies only with temperature, the improvement wherein said sheath is constructed of an oxygen ion conducting ceramic.

7. The system of claim 6, wherein the sheath is composed of at least one oxygen ion conducting ceramic selected from the group consisting of stabilized zirconium oxide, doped thorium oxide, doped cerium oxide and doped lanthanum oxide.

8. The system of claim 6, wherein the oxygen ion conducting ceramic is stabilized zirconium oxide.

9. The system of claim 8, wherein the stabilizing agent for the zirconium oxide is selected from the group consisting of yttria, scandia, calcia and magnesia.

10. The system of claim 6, wherein the electrochemical system consists of a silver-silver halide electrode located in the ceramic sheath, the halide of said silver halide is selected from the group of chloride, bromide and iodide, an electrically conducting lead in electrical contact with said silver-silver halide electrode extending from said ceramic sheath and a liquid solution of predetermined stable hydrogen ion concentration comprising a halide salt corresponding to that of said silver halide filling a portion of said ceramic sheath and contacting said ceramic sheath and said silver-silver halide electrode.

11. The system of claim 10, wherein the halide is chloride.

12. The system of claim 6, wherein the electrochemical system consists of a mixture of a metal and an oxide thereof and an electrically conducting lead extending from said ceramic sheath, said mixture filling a portion of said ceramic sheath and contacting said ceramic sheath and said lead.

13. The system of claim 12, wherein the metal employed is selected from the group consisting of copper, mercury, iron, nickel, and silver.

14. The system of claim 13, wherein the metal is copper and the oxide is cuprous oxide.

15. The system of claim 6, wherein the electrochemical system consists of a mixture of two different oxides of the same metal and an electrically conducting lead extending from said ceramic sheath, said mixture filling a portion of said ceramic sheath and contacting said ceramic sheath and said lead.

16. The system of claim 15, wherein the mixture is a mixture of ferrous oxide and magnetite.

* * * * *